United States Patent
Node-Langlois et al.

(10) Patent No.: US 10,872,690 B2
(45) Date of Patent: Dec. 22, 2020

(54) SYSTEM AND METHOD FOR REMOTE VISUALIZATION OF MEDICAL IMAGES

(71) Applicant: General Electric Company, Schenectady, NY (US)

(72) Inventors: Laurent Node-Langlois, Salt Lake City, UT (US); Julio-Gustavo Perez-Fernandez, Salt Lake City, UT (US)

(73) Assignee: General Electric Company, Schenectady, NY (US)

( * ) Notice: Subject to any disclaimer, the term of this patent is extended or adjusted under 35 U.S.C. 154(b) by 101 days.

(21) Appl. No.: 16/202,997

(22) Filed: Nov. 28, 2018

(65) Prior Publication Data
US 2020/0168318 A1    May 28, 2020

(51) Int. Cl.
| | | |
|---|---|---|
| G06K 9/00 | (2006.01) | |
| G16H 30/20 | (2018.01) | |
| A61B 90/00 | (2016.01) | |
| G16H 30/40 | (2018.01) | |
| A61B 6/03 | (2006.01) | |

(52) U.S. Cl.
CPC ............ *G16H 30/20* (2018.01); *A61B 6/032* (2013.01); *A61B 90/37* (2016.02); *G16H 30/40* (2018.01); *A61B 6/037* (2013.01); *A61B 90/361* (2016.02); *A61B 2090/374* (2016.02); *A61B 2090/376* (2016.02)

(58) Field of Classification Search
CPC ........ G06H 30/20; G06H 30/40; A61B 90/37; A61B 90/361; A61B 6/032; A61B 6/037; A61B 2090/374; A61B 2090/376
USPC ............................................... 358/128
See application file for complete search history.

(56) References Cited

U.S. PATENT DOCUMENTS

| | | | |
|---|---|---|---|
| 6,814,489 | B2 | 11/2004 | Jensen et al. |
| 7,281,213 | B2 | 10/2007 | Callegari |
| 2008/0068290 | A1 | 3/2008 | Muklashy et al. |
| 2012/0262379 | A1 | 10/2012 | King |
| 2012/0289825 | A1 | 11/2012 | Rai et al. |
| 2014/0016750 | A1 | 1/2014 | Kang et al. |
| 2014/0031664 | A1 | 1/2014 | Kang et al. |
| 2014/0064454 | A1 | 3/2014 | Hammond |
| 2014/0328517 | A1* | 11/2014 | Gluncic ............... A61B 8/5215 382/103 |
| 2015/0347682 | A1* | 12/2015 | Chen ..................... G16H 50/20 705/2 |

(Continued)

OTHER PUBLICATIONS

European patent application 19211671.3 filed Nov. 26, 2019; European Search Report dated Jan. 23, 2020; 11 pages.

*Primary Examiner* — Gabriel I Garcia

(57) ABSTRACT

A system for remote visualization of medical images is disclosed. The system comprises an imaging device for acquiring image data of an anatomy of a subject, and a display communicably coupled to the imaging device. The system also includes a mobile device communicating with the imaging device and the display over a dedicated communication channel, wherein the mobile device comprises one or more applications, wherein an application of the one or more applications is configured to receive the image data from one or more of the imaging device and the display, perform tomographic image reconstruction using the image data to generate a tomographic image and present the tomographic image to the user.

18 Claims, 7 Drawing Sheets

(56) References Cited

U.S. PATENT DOCUMENTS

| | | |
|---|---|---|
| 2016/0128654 A1 | 5/2016 | Wollowick |
| 2016/0296185 A1 | 10/2016 | Gemmel et al. |
| 2018/0116724 A1* | 5/2018 | Gmeiner ................ A61B 34/10 |
| 2018/0249975 A1 | 9/2018 | Brody |
| 2018/0360409 A1* | 12/2018 | Shen .................... G05D 1/0234 |
| 2019/0038356 A1* | 2/2019 | Schmitt ................. A61B 5/742 |

* cited by examiner

SYSTEM AND METHOD FOR REMOTE VISUALIZATION OF MEDICAL IMAGES

FIELD OF THE INVENTION

Embodiments of the present specification relate generally to a system and method for visualizing medical images, and more specifically to remote visualization of medical images through a mobile device.

BACKGROUND OF THE INVENTION

Medical practitioners, such as doctors, surgeons, and other medical professionals, often rely upon technology when performing a medical procedure, such as image-guided surgery or examination. In medical and surgical imaging, such as intraoperative or perioperative imaging, images are formed of a region of a patient's body. The images are used to aid in an ongoing procedure with a surgical tool or instrument applied to the patient and tracked in relation to a reference coordinate system formed from the images. Image-guided surgery is of a special utility in surgical procedures such as brain surgery and arthroscopic procedures on the knee, wrist, shoulder or spine, as well as certain types of angiography, cardiac procedures, interventional radiology and biopsies in which x-ray images may be taken to display, correct the position of, or otherwise navigate a tool or instrument involved in the procedure.

For almost all the surgical procedures, the surgery planning is done using pre-operative images which includes, may be for example X-ray, MRI, and CT images. The medical practitioner may perform measurements and annotations on these images in order to prepare and plan for the surgery or any other medical procedure. For example, before performing an anterior hip replacement procedure, the medical practitioner will use a pre-operative CT axial view image to determine the correct or appropriate size of prosthesis cups and location of the prosthesis. Thus, annotations and other information are added on to pre-operative images by the medical practitioner and stored into a database (for example, a hospital server). During the surgery, the medical practitioner may have access to an imaging device such as, a C-arm to locate the position of the prosthesis. For anterior hip replacement preformed on a subject (i.e. patient), the medical practitioner may need to verify physiological parameters, such as leg length of the subject and femoral neck offset. The medical practitioner only has limited options to confirm if the surgery is being done according to the plan, and these are by using a light box with the physical pre-operative images attached to it, using a standalone display or viewer to present the pre-operative imaged pulled from the server, or review a printed copy of the medical practitioner's plan for the surgery. In all these scenarios, the medical practitioner may have to leave the surgery room or pause the surgery. Thus, there exists a discontinuity between pre-operative planning by the surgeon and live surgery.

SUMMARY OF THE INVENTION

One embodiment of the present disclosure relates to a system for remote visualization of medical images. The system comprises an imaging system for acquiring image data of an anatomy of a subject, and a display communicably coupled to the imaging system. The system also includes a mobile device communicating with the imaging system and the display over a dedicated communication channel, wherein the mobile device comprises one or more applications, wherein an application of the one or more applications is configured to receive the image data from one or more of the imaging device and the display, perform tomographic image reconstruction using the image data to generate a tomographic image and present the tomographic image to the user.

In accordance with another aspect of the present disclosure, a method of visualizing images acquired by a medical imaging device is disclosed. The method involves providing the medical imaging device for acquiring image data of an anatomy of a subject, providing a display communicably coupled to the medical imaging device for displaying the images acquired by the medical imaging device, providing a mobile device communicating with the medical imaging device and the display over a dedicated communication channel; and providing one or more applications to operate in the mobile device, wherein an application of the one or more applications is configured to receive the image data from one or more of the medical imaging device and the display, perform tomographic image reconstruction using the image data to generate a tomographic image, and present the tomographic image to a user.

In accordance with yet another aspect of the present disclosure, a method of visualizing images acquired by a medical imaging device is disclosed. The method involves receiving a live image by an application in a mobile device communicably coupled to the medical imaging device and display over a dedicated communication channel, wherein the live image is acquired by the imaging device. The method also involves receiving a pre-operative image by the application from a database communicably coupled to the medical imaging device; and presenting the live image and the pre-operative image in the mobile device to a user.

A more complete understanding of the present disclosure, as well as further features and advantages thereof, will be obtained by reference to the following detailed description and drawings.

DETAILED DESCRIPTION OF THE INVENTION

Figure 1:
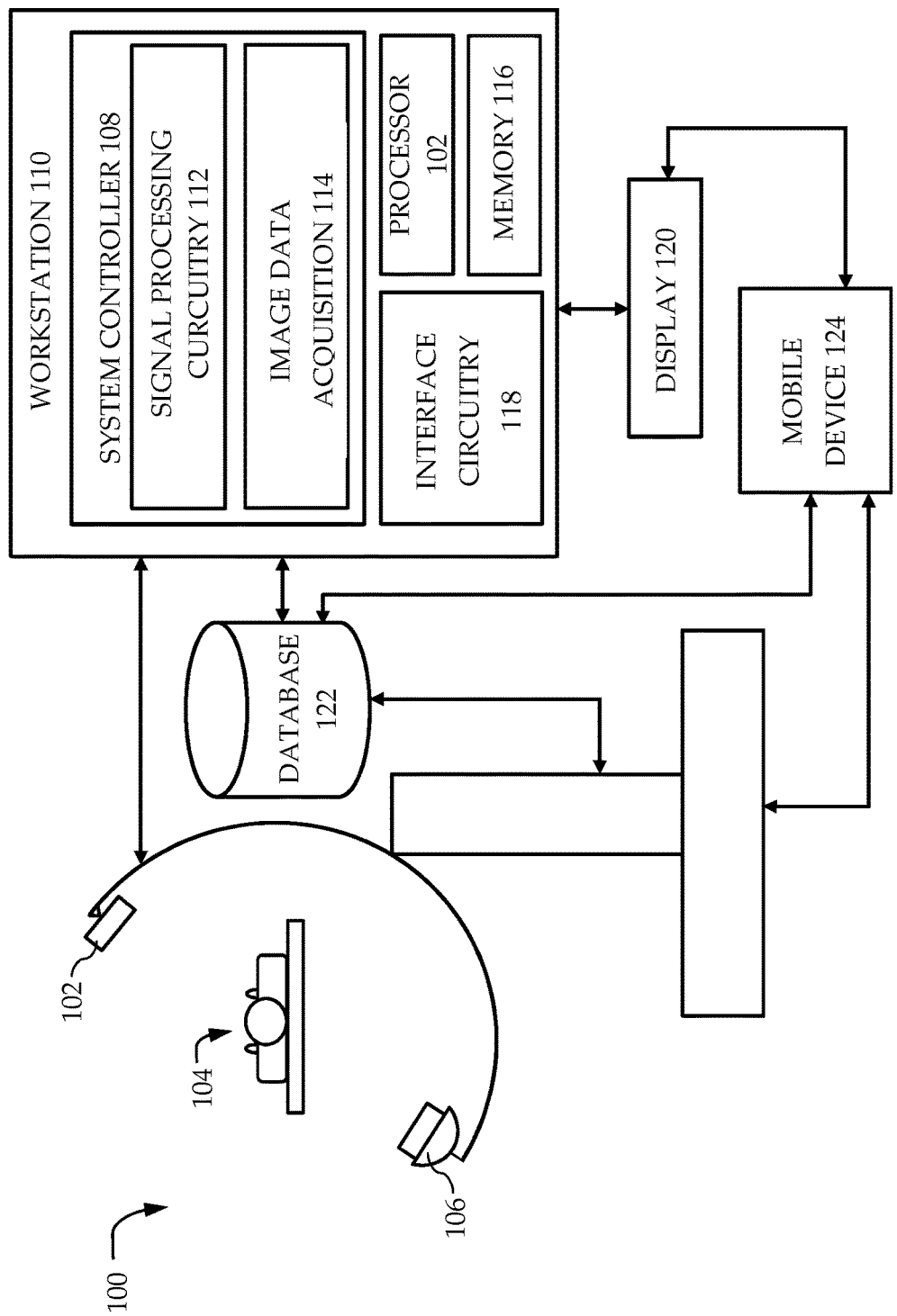
FIG. 1 illustrates an X-ray based imaging device for acquiring X-ray images or fluoroscopy images according to an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present disclosure are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In addition, it should be understood that references to "one embodiment" or "an embodiment" of the present disclosure are not intended to be interpreted as excluding the existence of additional embodiments that also incorporate the recited features. Further, the limitations of the following claims are not written in means-plus-function format and are not intended to be interpreted as such, unless and until such claim limitations expressly use the phrase "means for" followed by a statement of function void of further structure.

As discussed in detail below, embodiments of a system for remote visualization of medical images is disclosed. The system comprises an imaging device for acquiring image data of an anatomy of a subject, and a display communicably coupled to the imaging device. The system also includes a mobile device communicating with the imaging device and the display over a dedicated communication channel, wherein the mobile device comprises one or more applications, wherein an application of the one or more applications is configured to receive the image data from one or more of the imaging device and the display, perform tomographic image reconstruction using the image data to generate a tomographic image, and present the tomographic image to the user.

FIG. 1 shows schematically an X-ray based imaging device 100 for acquiring X-ray images or fluoroscopy images in accordance with the disclosure. The X-ray based imaging device 100 includes a source 102 of X-ray radiation positioned adjacent to a collimator (not shown in FIG. 1). The X-ray source 102 may be a standard X-ray tube or one or more solid-state X-ray emitters. The collimator permits a stream of radiation to pass into a region in which a subject, such as a patient 104, is positioned. During operation, a portion of the radiation passes through or around the patient 104 and impacts a detector array 106. Detector elements of the detector array 106 produce electrical signals that represent the intensity of the incident X-ray beam.

The source 102 is controlled by a system controller 108 of a workstation 110, which furnishes both power and control signals for examination procedures. Moreover, the detector array 106 is coupled to the system controller 108, which commands acquisition of the signals generated in the detector array 106. In general, system controller 108 commands operation of the X-ray based imaging device 100 to execute examination protocols and, in some embodiments, to process acquired data. The system controller 108 also includes signal processing circuitry 112, typically based upon a general purpose or application-specific digital computer, associated memory circuitry for storing programs and routines executed by the computer (such as programs and routines for implementing the present technique), as well as configuration parameters and image data, interface circuits, and so forth. Additionally, the system controller 108 may control the source 102 of radiation. Particularly, the system controller 108 may be configured to provide power and timing signals to the source 102.

The system controller 108 is also illustrated as including an image data acquisition system 114. In this embodiment, the detector array 106 is coupled to the system controller 108, and more particularly to the image data acquisition system 114. The image data acquisition system 114 receives data collected by readout electronics of the detector array 106. In one embodiment, the image data acquisition system 114 receives sampled analog signals from the detector array 106 and converts the data to digital signals for subsequent processing by a processing circuitry 112, which may, for example, be one or more processors of a general or application specific computer. The processing circuitry 112 along with the image data acquisition system 114 generates images by processing the digital signals.

The processing circuitry 112 may include (or may communicate with) a memory 116 that stores data processed by the processing circuitry 112 or data to be processed (such as fluoroscopic images produced by the imaging of patient 104 or position/orientation data) by the processing circuitry 112. It should be understood that any type of computer accessible memory device capable of storing the desired amount of data and/or code may be utilized by the imaging device 100. Moreover, the memory 116 may include one or more memory devices, such as magnetic, solid state, or optical devices, of similar or different types, which may be local and/or remote to the system 100. The memory 116 may store data, processing parameters, and/or computer programs having one or more routines for performing the processes described herein.

The imaging device 100 communicates with the workstation 110 through an interface circuitry 118. The images generated are presented through a display 120 communicably connected to the workstation 110. The imaging device 100 and the workstation 110 may be communicably connected to a database 122. The database 122 may include a plurality of images stored therein, where the plurality of images may include pre-operative images, and images acquired by the imaging device 100. The database 122 may be a database which is remotely located, or a storage device located locally near the imaging device 100. In an embodiment the database 122 may be part of a picture archiving and communication system (PACS) server in a hospital environment. A medical practitioner (e.g. surgeon or radiologist) adds annotations, measurements or markings in an image captured by the imaging device 100 to store as a preoperative image. Pre-operative images refer to images taken of a subject's anatomy prior to conducting a surgery for planning the surgery. The medical practitioner may need to access the pre-operative images while performing the surgical procedure. To this end, a mobile device 124 enables presentation of the pre-operative images received from the database 122 to the surgeon in the operating room. The mobile device 124 may be a smart phone, a tablet, a laptop, and so on. The mobile device 124 may be any off-the-shelf mobile device. Thus, the mobile device 124 may a personal mobile device of a user. The user may be for example, a surgeon, a medical practitioner and so on. As shown in FIG. 1, the mobile device 124 is communicably connected to the database 122 and the imaging device 100 over a dedicated communication channel. The dedicated communication channel is a secured channel that is dedicated for secure communication between the mobile device 124 and, the database 122 and the imaging device 100. The dedicated communication channel may be a wired or wireless communication channel or a combination thereof. The dedicated communication channel may be secured using security protocols known in the art. The mobile device 124 may be wirelessly connected to the database 122 and the imaging device 100. In an embodiment, the mobile device 124 may be connected to the database 122 and the imaging device 100 through a wired connection. However, it may be envisioned that the mobile device 124, database 122 and the display 120 may be connected to each other using any combination of wired or wireless connection.

In an embodiment, the mobile device 124 may present a live image based on image data of subject anatomy acquired by the imaging device 100. The live image may be for instance an image of the subject anatomy captured and transmitted to the mobile device 124 in real-time. For example, the live image may also include image captured by the imaging device 100 during the surgical procedure. In another embodiment, the live image may be generated from the image data acquired in real-time. The image data may be used to reconstruct a tomographic image in the mobile device and may be presented as the live image. The image data in this context may include image projections captured from multiple angles. The tomographic image is reconstructed from these image projections. The tomographic image is a three-dimensional image of the subject's anatomy. The live image may be also displayed through the display 120. In another embodiment, the live image presented in the display 120 may be directly transmitted to the mobile device 124 to be presented to the surgeon. In this context, the mobile device 124 is directly communicating with the display 120 to receive the live image. The communication between the mobile device 124 and the display 120 may be a wired or a wireless connection. This is further explained in detail in conjunction with FIG. 3. The surgeon may perform some procedural operations on the live image or the pre-operative images such as, adding annotations or markings and so on, and store them in the database 122. Thus, the procedural operations refer to modifications or additions performed on the images by the surgeon. The mobile device 124 helps the surgeon to view pre-operative images that assists in performing the surgical procedure and helps in conveniently storing any live image with annotations or markings and modified pre-operative images into a database (e.g. the database 122).

Figure 2:
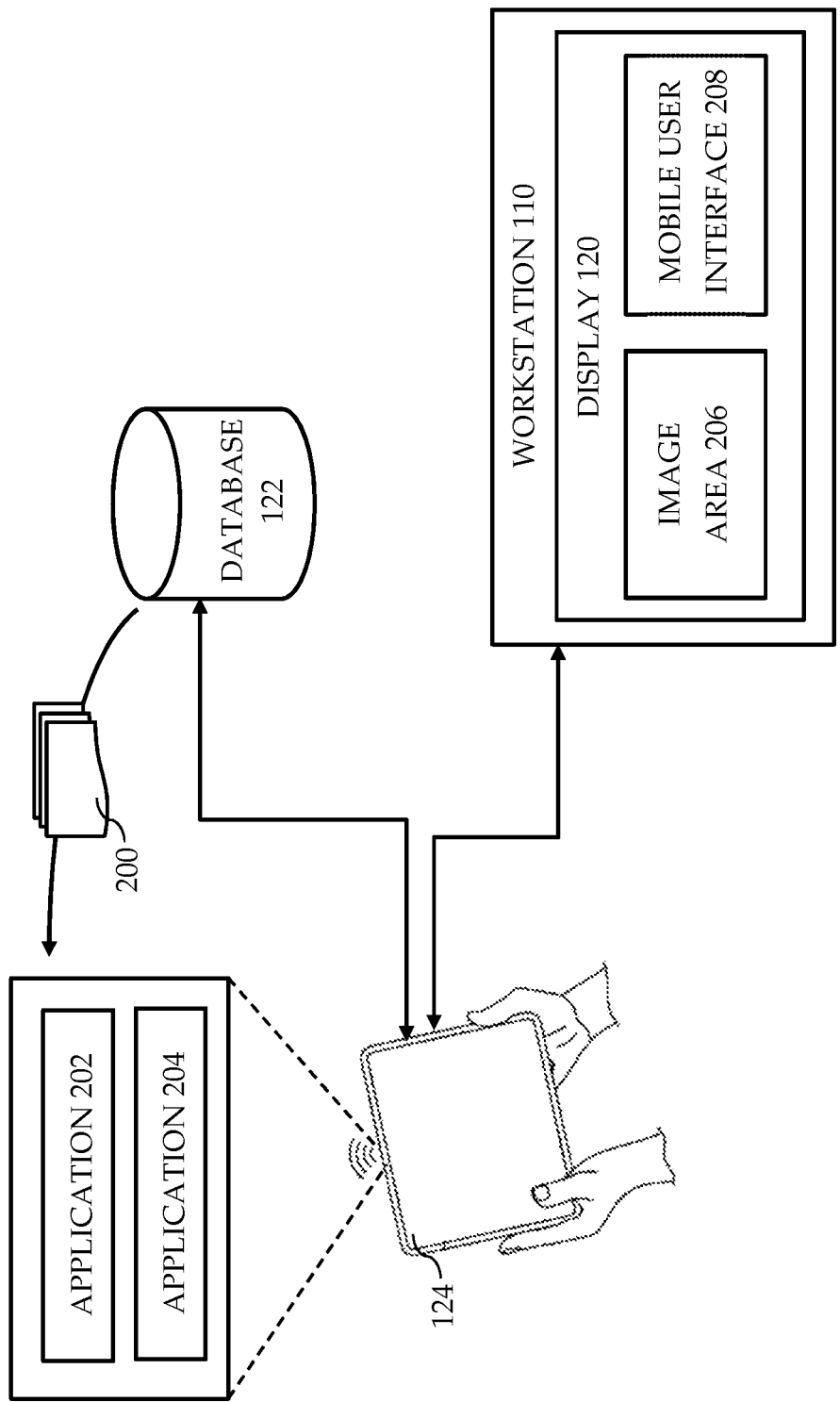
FIG. 2 illustrates communication between a mobile device, a database and a workstation according to an embodiment.

Moving on to FIG. 2 schematically illustrating communication between the mobile device 124, the database 122 and the workstation 110 according to an embodiment. The mobile device 124, the database 122 and the workstation 110 may be communicating with each other over a wired or wireless connection. The mobile device 124 receives pre-operative images 200 from the database 122. The mobile device 124 may send a request to the database 122 for the pre-operative images 200. The mobile device 124 may include multiple applications that may be used to present or process the pre-operative images 200. In an embodiment, the applications may be downloaded by the user from an application storage platform. The application storage platform may be hosted on a server. Alternatively, the applications may be preloaded in the mobile device 124. In an embodiment, the application may be a light application that operates in the mobile device 124. An application running in the mobile device 124 may facilitate to establish a dedicated communication channel between the mobile device 124 and the workstation 110 of the medical imaging device. In another instance, an application 202 may present a pre-operative image in the mobile device 124. The pre-operative image may be in a DICOM format. The application 202 enables the pre-operative image in the DICOM format to be presented in the mobile device 124. The medical practitioner may perform procedural operations such as, markings and annotations on the pre-operative images and a live image received from the workstation 110. The live image may be simultaneously presented in the display 120 and the mobile device 124. An application 204 may be used to perform procedural operations on the live image or the pre-operative image. The application 204 may be for example, an annotation tool, a marking tool and so forth.

Explaining by way of an example, the application 202 may be a DICOM viewing application that presents a pre-operative image with markings and annotations pertaining to leg length and femoral neck off-set. The surgeon can determine a right size and angle of a cup or prosthesis from the pre-operative image for an anterior hip replacement surgery. Moreover, by viewing the pre-operative images, the surgeon can conveniently verify the length of the leg and femoral neck off-set measurements for performing the surgery. A live image of the femur and the leg displayed in an image area 206 of the display 120, may be also presented in the mobile device 124. The surgeon can view the pre-operative image and the live image simultaneously in the mobile device 124 and confirm if the surgery is in conformity with the pre-operative planning. The application 204 (e.g. an annotation and viewing tool) may present the live image and enable the surgeon to add annotations and markings on the live image. The annotated or marked live image may be stored in the database 122. The mobile device 124 may include another application (not shown in FIG. 2) for storing the images in the database 122. Alternatively, the annotated or marked live image may be send by the application 204 to the database 122 for storage. In still another embodiment, the annotated or marked live image may be stored in the mobile device 124 by the application 204. It may be noted that even though only two applications namely, the application 202 and the application 204 are described in FIG. 2, there can be multiple other applications which can function in the mobile device 124 for performing various other operations within the scope of this disclosure. In another embodiment, the application 204 may be a tomographic image reconstruction application that can generate tomographic image(s) using image data that is received from a medical imaging device having the workstation 110. The image data may be captured in real-time by the medical imaging device. The image data may include image projections of an area of interest of the subject's anatomy at different angles. The tomographic image reconstruction application reconstructs the tomographic image(s) from the image projections.

The workstation 110 of the medical imaging device may present a mobile user interface 208 of the mobile device 124. The mobile user interface 208 refers to live presentation of images or content presented in the mobile device 124. Thus, the surgeon can see the images or content shown in mobile device 124 simultaneously in the workstation 110. This can provide a convenient way for other co-surgeons to observe images viewed and procedural operations performed on the images using the mobile device 124 by the surgeon.

Figure 3:
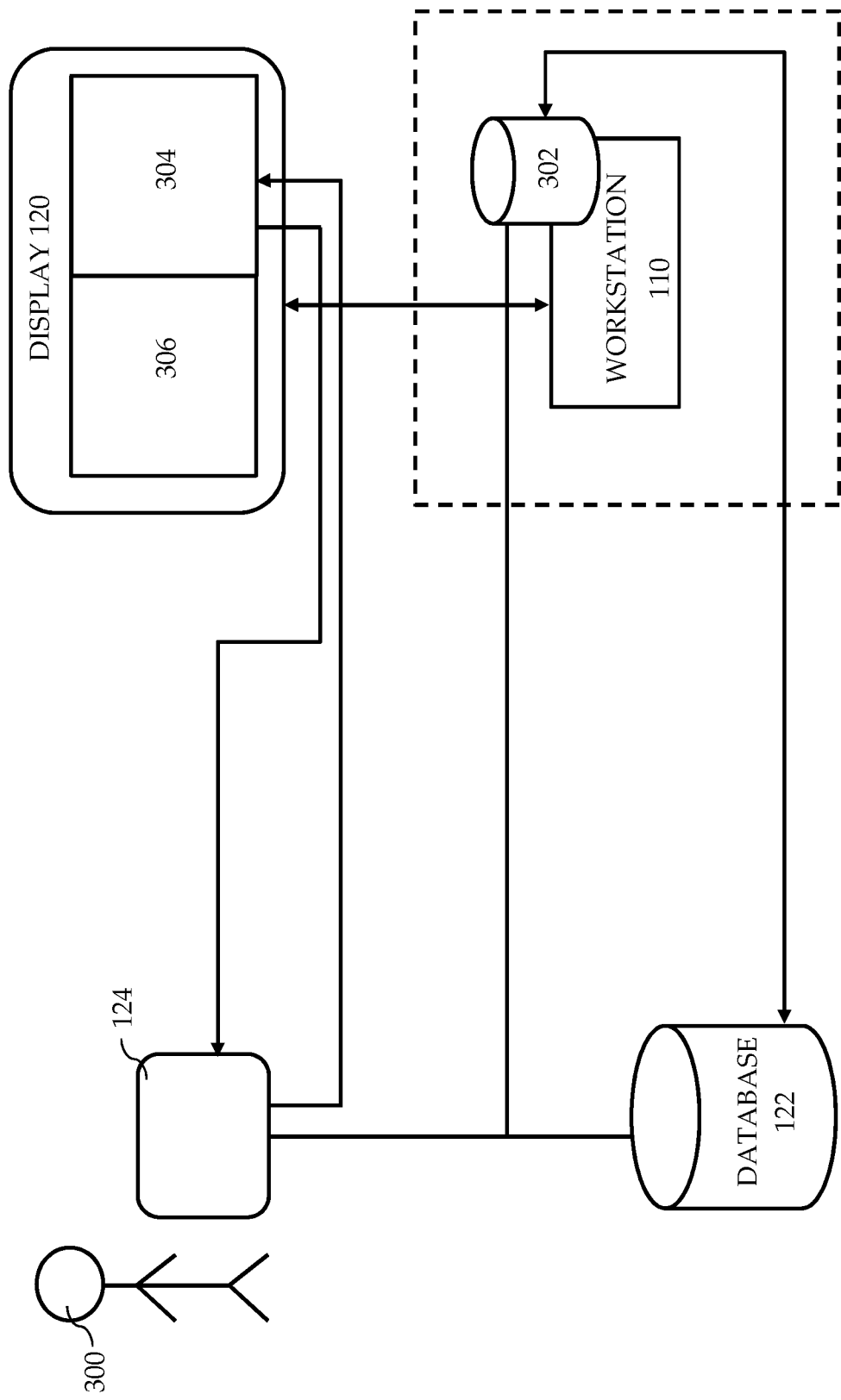
FIG. 3 illustrates a workflow diagram showing the interaction between the mobile device, the workstation, the display and the database according to an embodiment.

FIG. 3 schematically illustrates a workflow diagram showing the interaction between the mobile device 124, the workstation 110, the display 120 and the database 122 according to an embodiment. In a scenario, a user 300 uses the mobile device 124 to open an application that receives and loads pre-operative images stored in the database 122, prior to surgery. The user 300 may be a surgeon or any medical practitioner. The user 300 uses another application in the mobile device 124 to add annotations, measurements, markings and labeling in the pre-operative images. Thereafter, these updated pre-operative images are saved and send to database 122 for storage. In another embodiment, the updated pre-operative images may be send to a database 302 of the workstation 110. The database 302 may be of the imaging device 100. In this scenario, the user 300 may be at a remote location or outside of the operating room and can prepare and plan for surgery by viewing the pre-operative images. The updated pre-operative images may be presented in a right side 304 of the display 120. A left side 306 of the display 120 may present the live image captured of the subject's anatomy by the imaging device 100. The user 300 can view the updated pre-operative images and the live image side by side, which can help in performing the surgery according to the plan. Moreover, any pre-operative images received from the database 122 may be presented in the right side 304 of the display 120 while performing the surgery.

Considering another scenario, the user 300 is in the surgery room and using the mobile device 124. The mobile device 124 presents the pre-operative images and the updated pre-operative images needed for the user 300. The user interface of the mobile device 124 may be shown in the display 120. In an embodiment, the right side 304 of the display 120 presents the user interface (e.g. the mobile user interface 208) of the mobile device 124.

In an embodiment, content displayed in the display 120 may be presented in the mobile device 124. The content may include but are not limited to, user controls for controlling the operation of the imaging system (e.g. the imaging device 100), and other information associated with the pre-operative images. The user controls may be for example, image catalog, cine run, pause, device movement controls and so on. The user controls are used for example, accessing the pre-operative images, playing image cine, controlling the movement of imaging device 100, and so forth. In an embodiment, the right side 304 of display 120 may be presented in the mobile device 124 as a mirror image. In this case, the right side 304 may display the user controls and the information associated with pre-operative images and updated pre-operative images. The mirror image refers to presenting any content shown in the display 120 in real-time in the mobile device 124. Thus, the user 300 can control the functioning of imaging device 100 remotely.

In yet another scenario, the user 300 may access an application (such as the application 202 or the application 204) in the mobile device 124 while being outside the operating room or in a remote location. The application presented in the mobile device 124 may be mirrored or presented in the display 120. In an embodiment, the right side 304 of the display 120 may present the application. Thus, user 300 or co-surgeons or people present in operating room can view the application and the operations performed by the user 300 using the application, on the display 120.

In another scenario, the user 300 using the mobile device 124 may be in a remote location and can access a live image taken by the imaging device (e.g. the imaging device 100) and transfer the live image to the mobile device 124. Further, the mobile device 124 may also access the images stored in the database 302 remotely and transfer the images to the mobile device 124.

In yet another scenario, the mobile device 124 may receive image data stored in the database 302 or the medical imaging device. The image data includes image projections acquired by the medical imaging device from multiple angles. The mobile device 124 may have an application (i.e., a tomographic image reconstruction application) that processes the image data to generate a tomographic image. The application may be accessed and run by the user 300 to perform tomographic image reconstruction. In another embodiment, the application may automatically process the image data without input of the user 300 or the user 300 manually running the application.

It may be noted that even though only few scenarios are described here wherein the user 300 operates the mobile device 124 and how the mobile device 124 interacts or communicates with the workstation 110, the display 120 and the database 122, there are several other scenarios possible within the scope of this disclosure.

Figure 4:
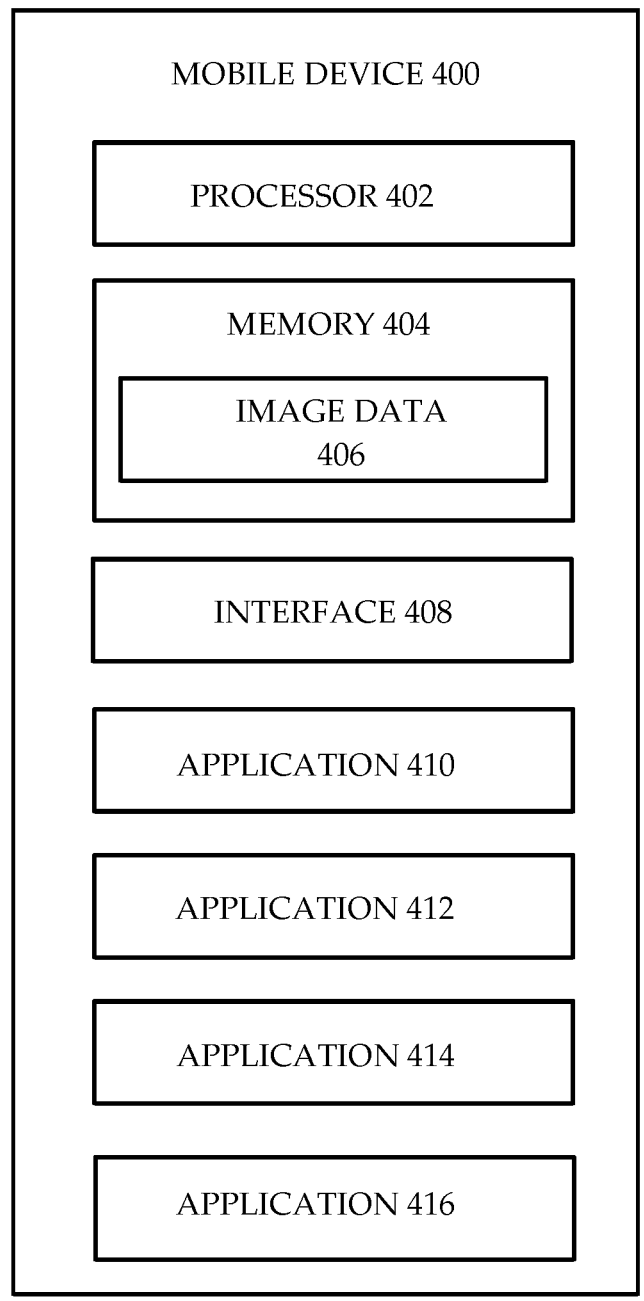
FIG. 4 illustrates a mobile device according to an embodiment.

Now referring to FIG. 4 illustrating a mobile device 400 according to an embodiment of the disclosure. The mobile device 400 described herein is similar to the mobile device 124 that communicates with a workstation and its display, an imaging system and a database described in conjunction with FIGS. 1-3. The mobile device 400 includes a processor 402, a memory 404 for storing image data 406 and an interface 408. The processor 402 enables the mobile device 124 to connect and communicate with the workstation and its display, the imaging system and the database. The processor 402 sends a request for pre-operative images to a database (e.g. the database 112). As a response, the processor 402 receives the pre-operative images and the interface 408 allows or enables access to these images for the applications present in the mobile device 400. As described earlier, in an embodiment the pre-operative images may be in a DICOM format. Alternatively, the pre-operative images may be in any other suitable imaging format. The interface 408 is an application program interface (API) that facilitates access to the pre-operative images in DICOM format for the applications e.g., applications 410, 412 and 414. The pre-operative images are processed by the application 410 which may be an annotation application based on user's input (e.g. input from the user 300). The application 410 adds annotations, markings, measurements and labels to a pre-operative image based on the user input to generate updated pre-operative images. The user is a surgeon or a medical practitioner. The updated pre-operative images may be send by the processor 402 to the database 112 for storing. Alternatively, the application 410 may send the updated pre-operative images to the database 112.

The pre-operative images and the updated pre-operative images are mirrored onto the display (e.g. the display 120) by another application 412 which may be a mirroring application. The application 412 may communicate with the processor 402 to access these images and mirror them based on user input. For instance, the user (e.g. the user 300) may access the application 412 to initiate mirroring of the images (e.g. the pre-operative images and the updated pre-operative images) in the display. The application 412 can be used for mirroring a user interface of the mobile device 400 to the display of the workstation. Moreover, in another embodiment, the application 412 can be used to mirror the display of the workstation on to the user interface of the mobile device 400. Thus, the content shown in the display can also be seen in the mobile device 400.

The images stored in the database may be processed to generate a three-dimensional tomographic image of the subject's anatomy. The mobile device 124 includes another application 414 that process these images to generate the three-dimensional tomographic image of the subject's anatomy based on user initiation. The processing performed by the application 414 involves three-dimensional tomographic reconstruction. The multiple images are captured by the imaging system (e.g. the imaging device 100) from different angles. More specifically, during image acquisition the imaging system moves around or spins around the subject to acquire multiple images of the subject's anatomy from different angles. These images are two-dimensional images. Once the images are captured they are stored in the database, and later received by the mobile device 124 based on request received from the application 414. The application 414 performs a three-dimensional tomographic image reconstruction process on multiple images to generate the three-dimensional image. The three-dimensional tomographic image of the subject's anatomy enables the user to confirm for example, position of implants in the subject's body after the surgery thereby avoiding performing a separate scan of the subject's body part.

The mobile device 124 also includes another application 416 that can establish a dedicated communication channel between the mobile device 124 and the medical imaging device and a display of the medical imaging device. The dedicated communication channel is a secured channel that is dedicated for secure communication between the mobile device 124 and, a database (e.g. the database 122) and the medical imaging device (e.g. the medical imaging device 100). The dedicated communication channel may be a wired or wireless communication channel or a combination thereof. The dedicated communication channel may be secured using security protocols known in the art. This dedicated communication channel enables secured transmission of images, commands and other data between the mobile device 124, the database and the medical imaging device.

Figure 5:
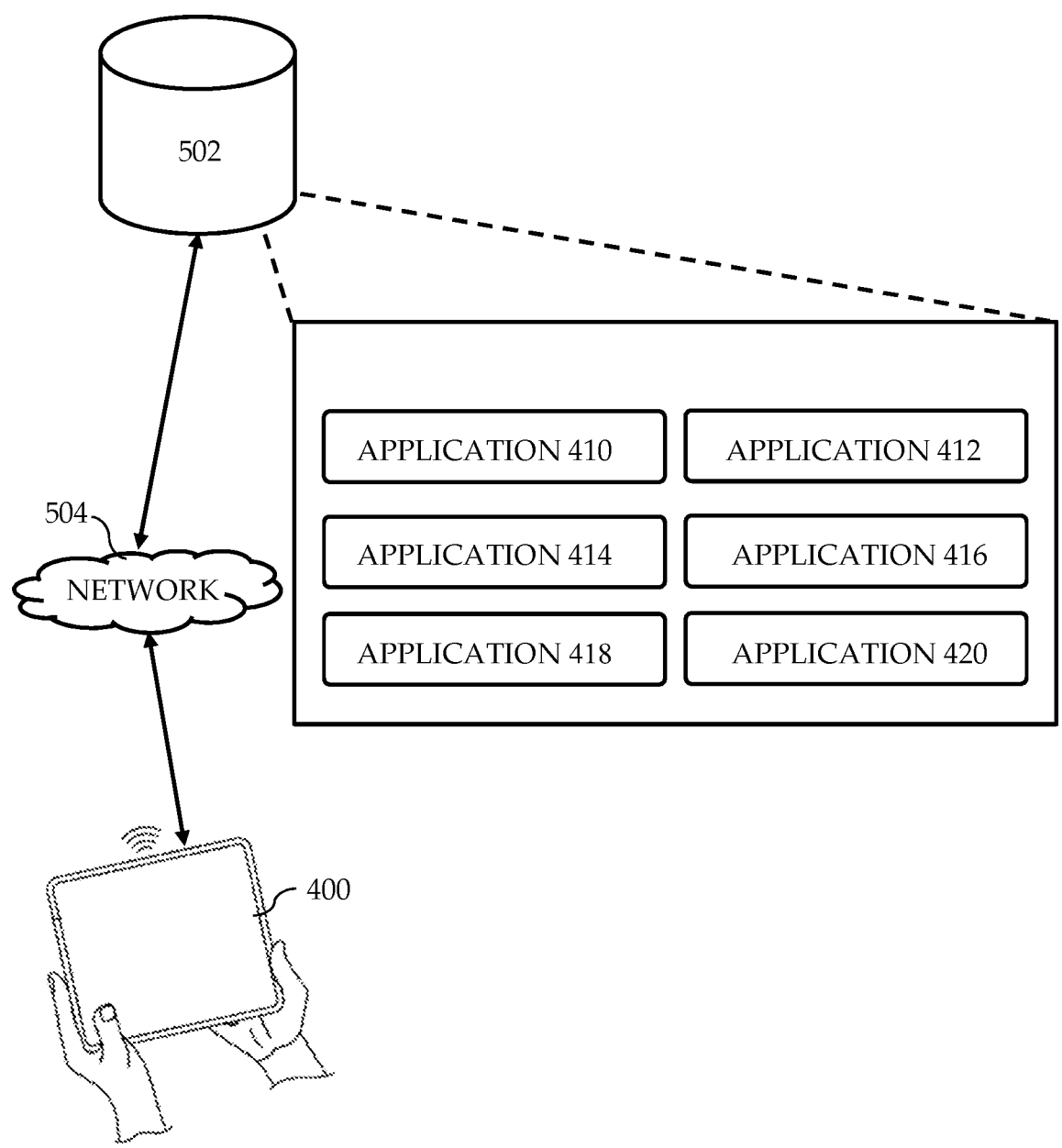
FIG. 5 illustrates a mobile device used to access applications from an application storage according to an embodiment.

The mobile device 124 may have numerous other applications functioning in it to perform various other functions even though only three applications and its functionalities are explained in FIG. 4. The user can download any application into the mobile device (e.g. the mobile device 400 or the mobile device 124) from an application storage and use them. FIG. 5 illustrates the mobile device 400 that is used to access applications from an application storage 502 according to an embodiment of the disclosure. The mobile device 400 communicates with the application storage 502 over a network 504. The network 504 may be, but are not limited to, internet (or any other wide area network), a wireless local area network, a personal area network, a wireless wide area network, a local area network and so on. The application storage 502 may be in an application server. In another embodiment, the application storage 502 may be platform such as GOOGLE PLAY® store. The application storage 502 may include numerous applications such as the applications 410, 412, 414, 416, 418 and 420. The applications may be provided by one or more third parties. The user may download desired third-party applications (such as the applications 410, 412 and 414) from the application storage 502 into the mobile device 400 for usage.

In another embodiment, the application storage 502 may be in a cloud based platform or a cloud based server and all applications may be running in this platform or server. The mobile device 400 connects to this platform and sends the images (such as the pre-operative images, the updated pre-operative images and the live images) to the cloud based platform or the cloud based server for processing by any desired applications. For example, the user can use an annotation application running in the cloud to add annotation, measurements and labels in the image, through the mobile device 400.

Figure 6:
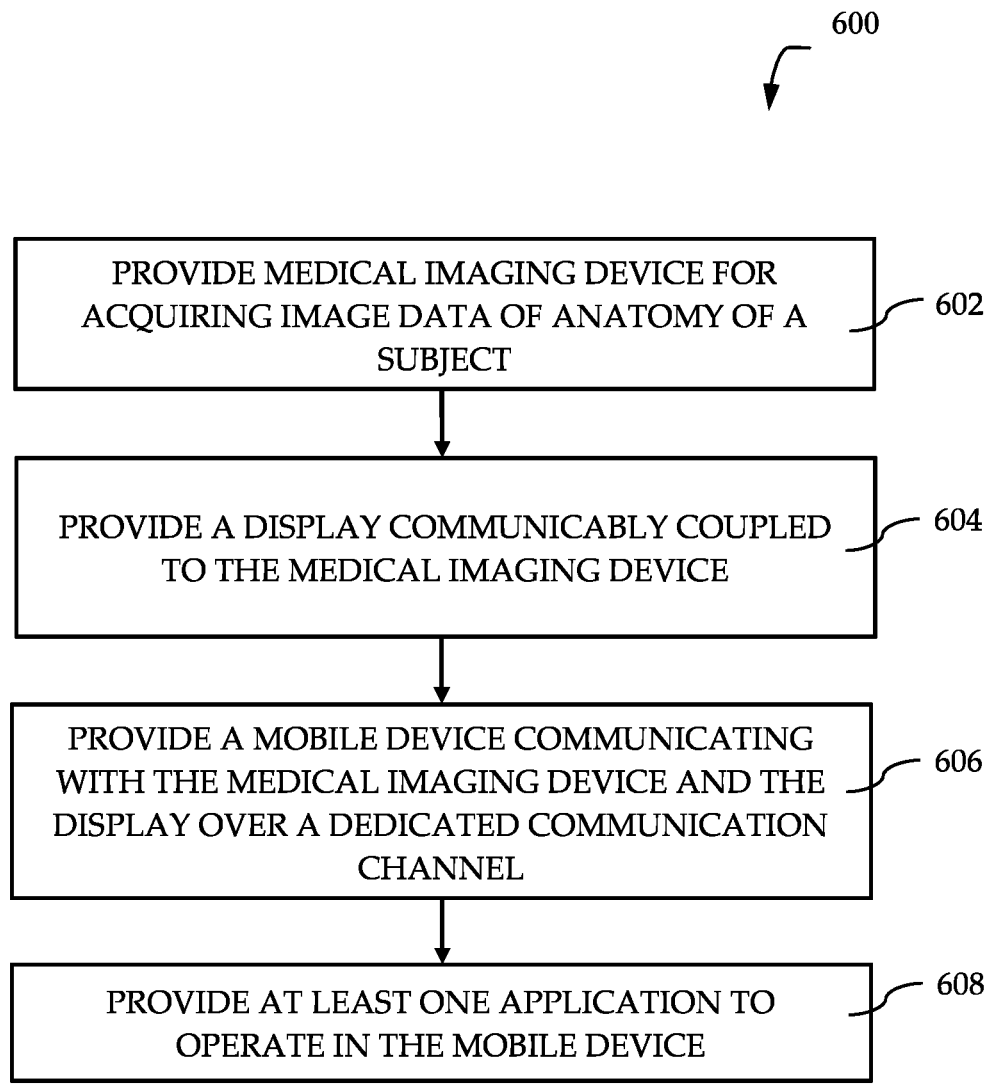
FIG. 6 illustrates a flow diagram of a method of visualizing images acquired by a medical imaging device according to an embodiment.

FIG. 6 illustrates a method 600 of visualizing images acquired by a medical imaging system according to an embodiment. The method 600 includes providing an imaging device for acquiring images of anatomy of a subject at step 602. A display communicably coupling to the imaging device is provided for displaying the images acquired from the imaging device at step 604. The display may be coupled to a workstation of the imaging device. The connection between the display and the workstation may be a wireless or a wired connection. A mobile device is provided that communicates with the imaging device and the display over a dedicated communication channel at step 606. The dedicated communication channel may be a wired or wireless connection. Then at step 608, one or more applications are provided that operate in the mobile device. The mobile device may receive pre-operative images stored in a database communicably coupled to the imaging device and the mobile device. An application running in the mobile device is configured to present a pre-operative image in the mobile device. Further, another application may receive an image (e.g. a live image) from one of the imaging device and the display and present the image to the user in the mobile device. The live image of subject's anatomy is acquired by the imaging device. The live image may be a tomographic image. Thus, the user can view the live image and the pre-operative image simultaneously in the mobile device.

In an embodiment, an application running in the mobile device can perform a procedural operation on an image (e.g. a pre-operative image or a live image) based on user's input. The procedural operations may include, but are not limited to, adding annotations, measurements, labels and so on in an image, and performing an image reconstruction such as, three-dimensional image reconstruction of the image. In an embodiment, a procedural operation such as annotating an image may be performed by an application. Further, another application may be used by the user to perform three-dimensional image reconstruction of the image. Because of performing the procedural operation on the image, a processed image may be generated. The processed image is send to the database for storage from the mobile device. In another embodiment, the processed image may be stored in the mobile device. The processed image can be projected on to the display connected to the imaging device. In an embodiment, a portion of the display connected to the imaging device may present the processed image. In another embodiment, content displayed in the mobile device may be presented on the display. The content can include but not limited to, the image (i.e. the live image and the pre-operative image), and the application used for performing procedural operations on the image. In an embodiment, user interface of the mobile device may be mirrored and presented in the display of the imaging device.

Figure 7:
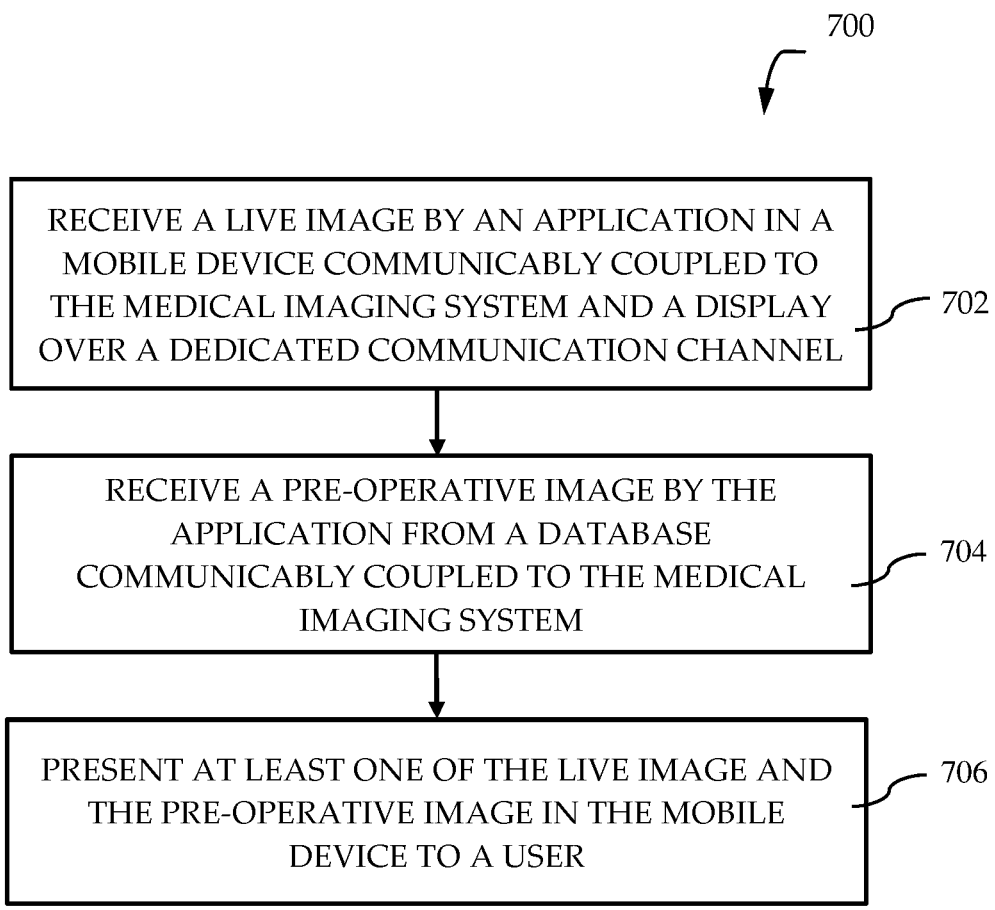
FIG. 7 illustrates a flow diagram of a method of visualizing images acquired by a medical imaging device according to an embodiment.

Now moving on to FIG. 7 illustrating a method 700 of visualizing the images acquired by a medical imaging system according to another embodiment. The method 700 involves receiving a live image by an application running or functioning in a mobile device (such as, the mobile device 124 and the mobile device 400) at step 702. The mobile device is communicably coupled to the medical imaging device and a display of the medical imaging device over a dedicated communication channel. The dedicated communication channel is a secured channel that is dedicated for secure communication between the mobile device, the database and the imaging device. The dedicated communication channel may be a wired or wireless communication channel or a combination thereof. The dedicated communication channel may be secured using security protocols known in the art. Then a pre-operative image is also received by the application from a database communicably coupled to the medical imaging device at step 704. The live image and the pre-operative image are presented through a user interface of the mobile device to the user at step 706. The user interface may be mirrored on the display of the medical imaging device. The user can perform procedural operations on the live image or the pre-operative image through the mobile device. The procedural operations may include, but are not limited to, adding annotations, measurements, labels and so on in an image, and performing an image reconstruction such as, three-dimensional image reconstruction of the image. Because of performing the procedural operation on the image, a processed image may be generated. The processed image is send to the database for storage from the mobile device.

Various embodiments of the systems and method for remote visualization of medical images. The system utilizes a mobile device connected with the imaging device (e.g. X-ray imaging device) and the display of the imaging device. The mobile device can be used to view a live image captured by the imaging device and a pre-operative image stored in a database (e.g. PACS) in a single screen by a surgeon. This helps the surgeon to refer to the pre-operative image and plan for the surgery. The surgeon can download third party applications in the mobile device for performing different procedural operations (e.g. annotation and three-dimensional image reconstruction) on the image (e.g. live image and pre-operative image). The mobile device provides access to the images captured by the imaging device to the third-party applications. A user interface of the mobile device or content displayed in the mobile device can be mirrored on to the display of the imaging device thereby making it convenient for the surgeon and co-surgeons to view what procedural operations are done by the surgeon on the images through the mobile device.

The above-described advantages should be regarded as illustrative rather than restrictive. It is to be understood that not necessarily all such objects or advantages described above may be achieved in accordance with any particular embodiment. Thus, for example, those skilled in the art will recognize that the systems and techniques described herein may be embodied or carried out in a manner that achieves or improves one advantage or group of advantages as taught herein without necessarily achieving other objects or advantages as may be taught or suggested herein.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem," "controller circuit," "circuit," or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "controller circuit".

The computer, subsystem, controller circuit, circuit executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, subsystem, controller circuit, and/or circuit to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general-computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects.

This written description uses examples to disclose the disclosure, including the best mode, and also to enable any person skilled in the art to practice the disclosure, including making and using any computing system or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A system comprising:
   an imaging device for acquiring image data of anatomy of a subject;
   a display communicably coupled to the imaging device; and
   a database communicable coupled to the imaging device, wherein the database stores one or more pre-operative images
   a mobile device communicably coupled to the database and communicating with the imaging device and the display over a dedicated communication channel, wherein the mobile device comprises at least one application, wherein an application of the at least one application is configured to:
     receive the image data from at least one of the imaging device and the display;
     perform tomographic image reconstruction using the image data to generate a tomographic image;
     present the tomographic image to a user;
     receive a preoperative image of the one or more pre-operative images; and
     present the received preoperative image to the user.

2. The system of claim 1, wherein the tomographic image is generated from the image data acquired live by the imaging device.

3. The system of claim 1, wherein the application of the at least one application is further configured to perform procedural operation on the tomographic image based on user input.

4. The system of claim 3, wherein the application of the at least one application is further configured to:
   generate a processed image based on the procedural operation performed on the image; and
   send the processed image to the database.

5. The system of claim 4, wherein the procedural operation comprises adding measurements and annotations to the image.

6. The system of claim 1, wherein the display is configured to present a user interface of the mobile device.

7. The system of claim 1, wherein the application of the at least one application is further configured to:
   present the tomographic image and the received preoperative image simultaneously.

8. The system of claim 1, wherein the display and the application of the at least one application are configured to:
   simultaneously display the tomographic image.

9. A method of visualizing images acquired by a medical imaging device, the method comprising:
   providing the medical imaging device for acquiring image data of anatomy of a subject;
   providing a display communicably coupled to the medical imaging device;
   providing a mobile device communicating with the imaging device and the display over a dedicated communication channel;
   providing at least one application to operate in the mobile device, wherein an application of the at least one application is configured to:
     receive the image data from at least one of the imaging device and the display;
     perform tomographic image reconstruction using the image data to generate a tomographic image;
     present the tomographic image to a user; and
     perform a procedural operation on the tomographic image based on a user input, wherein the procedural operation comprises adding measurements or annotations to the image.

10. The method of claim 9, further comprising providing a database communicably coupled to the imaging device and the mobile device, wherein the database stores pre-operative images, wherein the application is further configured to receive and present a preoperative image of the pre-operative images in the mobile device.

11. The method of claim 9, wherein performing the tomographic image reconstruction comprises generating the tomographic image from the image data acquired live by the imaging device.

12. The method of claim 11 further comprising:
    generating a processed image based on the procedural operation performed on the image; and
    sending the processed image to the database.

13. The method of claim 12 further comprising presenting a user interface of the mobile device in the display.

14. A method of visualizing images acquired by a medical imaging device, the method comprising:
    receiving a live image by an application in a mobile device communicably coupled to the medical imaging device and a display over a dedicated communication channel, wherein the live image is acquired by the medical imaging device;

receiving a pre-operative image by the application from a database communicably coupled to the medical imaging device; and presenting at least one of the live image and the pre-operative image in the mobile device to a user.

15. The method of claim 14 further comprising mirroring a user interface of the mobile device onto the display.

16. The method of claim 14 further comprising:

performing a procedural operation on the live image by the application based on user input;

generating a processed image based on the procedural operation; and sending the processed image to the database.

17. The method of claim 16, wherein the procedural operation comprises adding measurements and annotations to the image.

18. The method of claim 14 wherein the live image is a tomographic image.

* * * * *